(12) United States Patent
Flohr (10) Patent No.: US 9,439,617 B2
(45) Date of Patent: Sep. 13, 2016

(54) TOMOGRAPHIC IMAGING WITH ASYMMETRIC DETECTION

(71) Applicant: SIEMENS AKTIENGESELLSCHAFT, Munich (DE)

(72) Inventor: Thomas Flohr, Uehlfeld (DE)

(73) Assignee: Siemens Aktiengesellschaft, Munich (DE)

( * ) Notice: Subject to any disclaimer, the term of this patent is extended or adjusted under 35 U.S.C. 154(b) by 2 days.

(21) Appl. No.: 14/029,941

(22) Filed: Sep. 18, 2013

(65) Prior Publication Data

US 2014/0093031 A1    Apr. 3, 2014

(30) Foreign Application Priority Data

Oct. 1, 2012 (DE) .................. 10 2012 217 888

(51) Int. Cl.
*A61B 6/00* (2006.01)
*A61B 6/03* (2006.01)

(52) U.S. Cl.
CPC ............. *A61B 6/5235* (2013.01); *A61B 6/032* (2013.01); *A61B 6/4233* (2013.01)

(58) Field of Classification Search
CPC ...... A61B 6/025; A61B 6/027; A61B 6/032; A61B 6/4233; A61B 6/5235
See application file for complete search history.

(56) References Cited

U.S. PATENT DOCUMENTS

| | | | |
|---|---|---|---|
| 6,327,326 B1 | 12/2001 | Flohr et al. | |
| 7,372,939 B2 * | 5/2008 | Nabatame | .......... 378/19 |
| 8,553,833 B2 * | 10/2013 | Flohr et al. | .......... 378/15 |
| 2006/0159220 A1 | 7/2006 | Heuscher | |
| 2008/0049891 A1 | 2/2008 | Yin | |
| 2011/0317901 A1 | 12/2011 | Allmendinger et al. | |
| 2012/0014502 A1 | 1/2012 | De Man | |

FOREIGN PATENT DOCUMENTS

| | | |
|---|---|---|
| CN | 1919141 A | 2/2007 |
| CN | 102376097 A | 3/2012 |
| CN | 102393528 A | 3/2012 |
| DE | 19854438 A1 | 6/2000 |
| DE | 102010013361 A1 | 10/2011 |
| DE | 102010024684 A1 | 12/2011 |
| DE | 102012202499 A1 | 8/2013 |

OTHER PUBLICATIONS

Chinese Office Action for CN Patent Application No. 2013104354693 dated Apr. 20, 2015 and English translation.

* cited by examiner

*Primary Examiner* — Jack Berman
(74) *Attorney, Agent, or Firm* — Harness, Dickey & Pierce, P.L.C.

(57) ABSTRACT

A recording unit is rotatable about an axis of rotation, and includes an X-ray emitter and detector to detect X-rays from a fan-shaped region. The fan-shaped region is asymmetrical in relation to a vertical to the axis of rotation, running through the X-ray detector wherein the two edges of the fan-shaped region, on rotation, in each case tangentially delimit a first projection region and a second projection region. The second projection region abuts the first projection region. A method includes recording projections of the two projection regions during a full rotation of the recording unit for the reconstruction of a first image of the first projection region in such a way that the projection angle intervals in each case exhibit the same start angle. It further includes reconstructing a second image of the second projection region to merge the two reconstructed projection regions to form one unitary image.

19 Claims, 5 Drawing Sheets

TOMOGRAPHIC IMAGING WITH ASYMMETRIC DETECTION

PRIORITY STATEMENT

The present application hereby claims priority under 35 U.S.C. §119 to German patent application number DE 102012217888.0 filed Oct. 1, 2012, the entire contents of which are hereby incorporated herein by reference.

FIELD

At least one embodiment of the invention generally relates to a method and/or a system for tomographic imaging.

BACKGROUND

Computed tomography (CT) is an imaging method with which X-ray projections (in this case synonymous with "projections") are recorded at various different projection angles. In this situation, a recording unit, including an X-ray emitter and an X-ray detector, rotates about an axis of rotation. At the present time, most X-ray detectors of CT devices exhibit several lines along the axis of rotation. They also cover a large area inside the plane of rotation. Due to the fact that X-ray detectors for CT devices are expensive, the intention is that their surface, taking account of performance parameters such as the spatial resolution, should be kept relatively small.

One known possibility for reducing the size of the detector surface is for the detector to be asymmetrical in shape. The reconstruction of images on the basis of X-ray projections which are recorded with such asymmetrical detectors, however, imposes high demands. For the recording of moved structures in particular, such as the beating heart, the demands are particularly high. Specifically, the rotation of the recording unit takes approximately half a second to a second. When recording with an asymmetrical detector, not all the points inside the volume which it is intended should be reconstructed will necessarily contribute to every X-ray projection. Accordingly, for the reconstruction of different points, different X-ray projections must be used, which cover different areas and are therefore temporally skewed.

From the patent application with the application reference DE 102012202499.9, the entire contents of which are hereby incorporated herein by reference, a CT device is known which exhibits a gantry as well as an X-ray source and a detector, wherein the detector exhibits on at least one of its wide sides a side region which exhibits a lesser width than the overall width of the detector, wherein the lateral region, in relation to the overall width of the detector, is arranged offset to the middle. The CT device further exhibits a control apparatus, which, with spiral CT imaging, controls a gantry rotation and a detector advance relative to the volume which is to be imaged, co-ordinated in such a way that a direction of rotation of the gantry rotation and a direction of advance of the detector are matched to one another.

SUMMARY

At least one embodiment of the invention is directed to a method of improving the reconstruction of CT images on the basis of X-ray projections which have been taken with an asymmetric detection.

A method and a system are disclosed.

Features, advantages, or alternative embodiments are likewise to be transferred to other claimed objects, and vice-versa. In other words, the claims forming the object which relate, for example, to a system, can also be further developed with the features which are described or claimed in connection with a method. The corresponding functional features of the method are in this situation formed by corresponding object modules.

At least one embodiment of the invention makes use of a recording unit, rotatable about an axis of rotation, including an X-ray emitter and an X-ray detector, arranged such as to detect X-rays from a fan-shaped region, wherein the fan-shaped region is asymmetrical in relation to a vertical to the axis of rotation, running through the X-ray detector, wherein the two edges of the fan-shaped region, on rotation, in each case tangentially delimit a first projection region and a second projection region, wherein the second projection region abuts the first projection region.

At least one embodiment of the invention is based on the idea that a recording of projections of the two projection regions during a full rotation of the recording unit is used for the reconstruction of a first image of the first projection region in such a way that the projection angle intervals for the reconstruction of the points in the first image exhibit in each case the same start angle and therefore a concordant phase, which is of advantage in particular for the imaging of moved structures, such as, for example, the heart.

At least one embodiment of the invention is further based on the idea of making use of the recording for the reconstruction of a second image of the second projection region, wherein the start angle for the reconstruction of a point in the second image is selected based on a projection angle interval and based on the position of the respective point. The full rotation of the recording unit therefore also allows for the reconstruction of the outer second projection region, which is only detected in a part fan-shaped geometry, in different ways, in particular with an optimized time resolution. This allows for the reconstruction of CT data of asymmetrically detected X-ray projections to be substantially improved, inasmuch as the possibilities are extended for the application of different reconstruction algorithms in the two projection regions. At least one embodiment of the invention further allows for the two images of the reconstructed projection regions to be merged into one unitary image, which facilitates the interpretation of the images, in particular for diagnostic purposes.

At least one embodiment of the invention further comprises a system for tomographic imaging, including a recording unit, rotatable about an axis of rotation, including an X-ray emitter and an X-ray detector, arranged such as to detect X-rays from a fan-shaped region, wherein the fan-shaped region is asymmetrical in relation to a vertical to the axis of rotation, running through the X-ray detector, wherein the two edges of the fan-shaped region, on rotation, in each case tangentially delimit a first projection region and a second projection region, wherein the second projection region abuts the first projection region, wherein the recording unit is arranged for the recording of projections of the two projection regions during at least one full rotation.

BRIEF DESCRIPTION OF THE DRAWINGS

The invention is described and explained in greater detail hereinafter on the basis of the exemplary embodiments represented in the figures.

These show:

FIG. 1 an extended system for tomographic imaging,
FIG. 2 an asymmetric X-ray detector,
FIG. 3 a recording unit with projection regions in cross-section,
FIG. 4 a recording unit with a start angle in cross-section.

DETAILED DESCRIPTION OF THE EXAMPLE EMBODIMENTS

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

At least one embodiment of the invention makes use of a recording unit, rotatable about an axis of rotation, including an X-ray emitter and an X-ray detector, arranged such as to detect X-rays from a fan-shaped region, wherein the fan-shaped region is asymmetrical in relation to a vertical to the axis of rotation, running through the X-ray detector, wherein the two edges of the fan-shaped region, on rotation, in each case tangentially delimit a first projection region and a second projection region, wherein the second projection region abuts the first projection region.

At least one embodiment of the invention is based on the idea that a recording of projections of the two projection regions during a full rotation of the recording unit is used for the reconstruction of a first image of the first projection region in such a way that the projection angle intervals for the reconstruction of the points in the first image exhibit in each case the same start angle and therefore a concordant phase, which is of advantage in particular for the imaging of moved structures, such as, for example, the heart.

At least one embodiment of the invention is further based on the idea of making use of the recording for the reconstruction of a second image of the second projection region, wherein the start angle for the reconstruction of a point in the second image is selected based on a projection angle interval and based on the position of the respective point. The full rotation of the recording unit therefore also allows for the reconstruction of the outer second projection region, which is only detected in a part fan-shaped geometry, in different ways, in particular with an optimized time resolution. This allows for the reconstruction of CT data of asymmetrically detected X-ray projections to be substantially improved, inasmuch as the possibilities are extended for the application of different reconstruction algorithms in the two projection regions. At least one embodiment of the invention further allows for the two images of the reconstructed projection regions to be merged into one unitary image, which facilitates the interpretation of the images, in particular for diagnostic purposes.

At least one embodiment of the invention further comprises that, during the reconstruction of a point in the second image, the projection angle interval is selected in such a way that all the projections to which the respective point contributes are used for the reconstruction of the point. Accordingly, the data volume is maximized which is available for the reconstruction of a point in the second image.

At least one embodiment of the invention further comprises that, for the reconstruction of a point in the second image, the projection angle interval is delimited by two complementary projections of the respective point, and is selected as small as possible. In this case, the time resolution for the respective reconstructed point is optimized.

At least one embodiment of the invention further comprises that, for the reconstruction of a point in the second image, the length of the projection angle interval lies between the lengths of the two projection angle intervals referred to heretofore.

At least one embodiment of the invention further comprises that the first and the second images are merged to form one overall image.

At least one embodiment of the invention further comprises the reconstruction of a third image of the first projection region, wherein, for the reconstruction of a point in the third image, the projection angle interval is selected as corresponding to one of the projection angle intervals referred to heretofore. In particular, the points in the third image can be reconstructed with the aid of a minimum projection angle interval, such that they present an optimum time resolution.

At least one embodiment of the invention further comprises the adding of the first and the third image in accordance with a weighting function, wherein the added image and the second image are merged to form one overall image. In other words, at least one embodiment of the invention allows for the points in the first projection region, recorded under a full fan-shaped geometry, to be recorded for a first time with the same phase and for another time with optimized time resolution, and that these two reconstructions of the first projection region are added together, i.e. overlaid. The weighting function now allows for the determination of which points should exhibit a higher time resolution or a higher phase consistency respectively.

At least one embodiment of the invention further comprises that the weighting function weights points from the third image more strongly as the distance interval from the axis of rotation increases. If the second image of the second projection region and the third image of the first projection region have been reconstructed in each case with optimum time resolution, it is then possible with the invention for both projection regions to be reconstructed in such a way, and merged to form one overall image, that a continuous transition, as free of artefacts as possible, is obtained between the two projection regions.

At least one embodiment of the invention further comprises that several fourth images of the first projection region with different start angles in each case are reconstructed. The temporally displaced fourth images can be drawn on for the optimization of the position of the reconstruction interval in the heart cycle of the patient.

At least one embodiment of the invention further comprises that the recording is made in the form of a spiral scan with a pitch <0.5, such that a more complete data record for each image point is recorded in the second projection region.

At least one embodiment of the invention further comprises that the recording is triggered by an EKG signal of a patient, whereby the invention can be particularly favorably used for the imaging of the heart of the patient.

At least one embodiment of the invention further comprises a system for tomographic imaging, including a recording unit, rotatable about an axis of rotation, including an X-ray emitter and an X-ray detector, arranged such as to detect X-rays from a fan-shaped region, wherein the fan-shaped region is asymmetrical in relation to a vertical to the axis of rotation, running through the X-ray detector, wherein the two edges of the fan-shaped region, on rotation, in each case tangentially delimit a first projection region and a second projection region, wherein the second projection region abuts the first projection region, wherein the recording unit is arranged for the recording of projections of the two projection regions during at least one full rotation.

The system according to at least one embodiment of the invention further comprises a reconstruction unit, arranged for the reconstruction of a first image of the first projection region, in such a way that the projection angle intervals for the reconstruction of the points in the first image in each case exhibit the same start angle, and are arranged for the reconstruction of a second image of the second projection region, wherein the start angle for the reconstruction of a point in the second image is selected based on a projection angle interval and based on the position of the respective point. The system according to at least one embodiment of the invention further includes an image processing unit, arranged such as to merge two reconstructed images to form one overall image of the first and second projection regions.

At least one embodiment of the invention further comprises that the X-ray detector is subdivided by the vertical into two differently shaped and/or differently sized detector regions. Accordingly, the system according to at least one embodiment of the invention is particularly well-suited for carrying out one of the methods according to at least one embodiment of the invention, since such an X-ray detector is arranged for the asymmetric detection of two projection regions.

At least one embodiment of the invention further comprises that at least one detector region exhibits on its wide side a side region which, in the direction of the longitudinal axis, exhibits a lesser expansion than the remaining larger part of the detector region.

The system and its further embodiments are also arranged such as to carry out the methods according to at least one embodiment of the invention in an advantageous manner.

Figure 1:
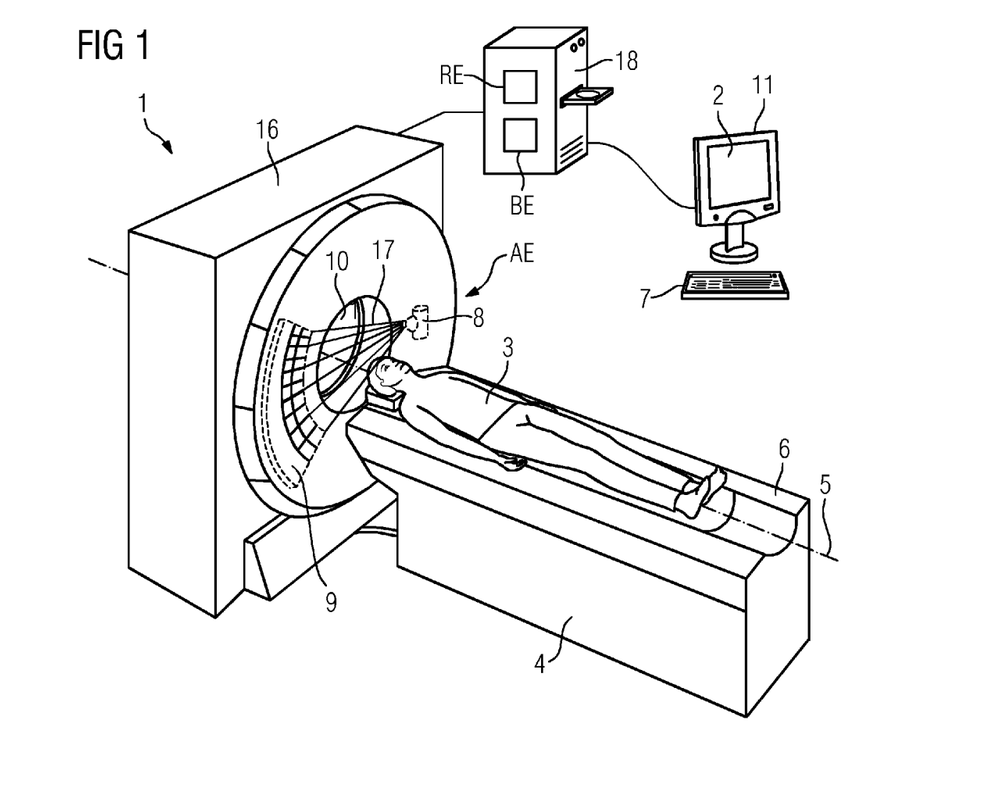

FIG. 1 shows an extended system for tomographic imaging. It comprises the system according to an embodiment of the invention, and can in particular be used for carrying out the method for tomographic imaging according to an embodiment of the invention.

The system serves to make a record A of projection data and the reconstruction and further processing of the projection data, in order to generate an image, in particular an image for medical purposes such as diagnosis. In this situation the system serves to record an (X-ray) image. Such an image can represent a surface as well as a volume. Accordingly, two-dimensional imaging can be carried out and formed from what are referred to as pixels, or three-dimensional imaging formed from what are referred to as voxels. In addition, an image in the meaning of the present application can extend not only spatially but also temporally. An image can therefore also comprise reconstructions of a temporal series of individual records, which in each case have been recorded at different points in time. This is particularly important if it is intended that conclusions should be drawn from the temporal change of a process which can be acquired by images, such as, for example, the flooding of a contrast medium.

With the recording A, the patient 3 lies on a patient couch 6, which is connected to a couch base 4 in such a way that it carries the patient couch 6 with the patient 3. For the recording A, the patient couch 6 can move the patient 3 along the axis of rotation 5 of the recording unit AE through the opening 10 of the gantry 16 of a CT device 1. In the example shown here, the axis of rotation 5 also corresponds to the longitudinal axis of the patient 3. The recording A of an X-ray image with the movement of the patient couch 6 is also referred to as a scan. For the recording A of a three-dimensional CT image, the recording unit AE rotates, including an X-ray emitter 8 and an X-ray detector 9, about the opening 10 of the CT device 1 and therefore about the axis of rotation 5, on a closed trajectory. The recording plane is the plane in which the recording unit AE rotates during the recording A. In the example shown in FIG. 1, the recording plane stands vertically on the longitudinal axis of the patient 3. The recording plane can, however, be arranged inclined in relation to the longitudinal axis of the patient 3, for example by an inclination of the patient couch 6 or by the inclination of the recording unit AE.

The X-ray emitter 8 is typically an X-ray tube; the X-ray detector 9 is typically a line detector or flat detector, but can also be arranged as a scintillator counter or CCD camera.

In particular, such an X-ray detector 9 can exhibit a scintillator ceramic. The X-ray emitter 8 and X-ray detector 9 are arranged in a gantry 16 in such a way that they are located opposite one another, and the X-rays 17, which the X-ray emitter 8 emits in a fan-shaped region 19, are detectable by the X-ray detector 9. In this situation, the fan-shaped region 19 is asymmetric in relation to a vertical 21 to the axis of rotation 5, running through the X-ray detector 9. The two edges of the fan-shaped region 19 in each case delimit, on rotation, an inner first projection region 14 and an outer second projection region 15 tangentially, wherein the second projection region 15 abuts the first projection region 14. In this situation, the inner first projection region 14 is detected in full-fan geometry, and the outer second projection region in part-fan geometry.

The recordings of the CT device 1 are sent to a computer 18 for processing and/or display. The computer 18 is further equipped with a reconstruction unit RE and an image processing unit BE. The reconstruction unit RE is arranged for the reconstruction of a first image R1 of the first projection region 14 in such a way that the projection angle intervals for the reconstruction of the points in the first image in each case exhibit the same start angle α, and are arranged for the reconstruction of a second image R2 of the second projection region 15, wherein the start angle α for the reconstruction of a point in the second image is selected on the basis of a projection angle interval and on the basis of the position of the respective point. The imaging unit BE is arranged for the merging Z of two images and for the adding AD of two images in accordance with a weighting function.

Both the reconstruction unit RE as well as the image processing unit BE can be formed as hardware or software. Both the reconstruction unit RE as well as the image processing unit BE can be implemented on different computers 18. For example, the image processing unit BE is formed as part of a server, while the reconstruction unit RE is formed as part of a local computer 18, which also serves to control the CT device 1. For example, the reconstruction unit RE can, at least partially, be formed as what is referred to as an FPGA (acronym for "Field Programmable Gate Array"), or comprise an arithmetic logic unit.

The computer 18 is connected to an output unit 11 and to an input unit 7. The output unit 11 is, for example, an (or several) LCD, plasma, or OLED screen(s). On the display unit 11 an output 2 is displayed, for example an X-ray image. The input unit 7 is, for example, a keyboard, a mouse, what is referred to as a touchscreen, or even a microphone for speech input. The input unit 7 can be used to start a program which actuates the reconstruction unit RE, the image processing unit BE, and the recording unit AE, and can therefore control the method described hereinafter.

Figure 2:
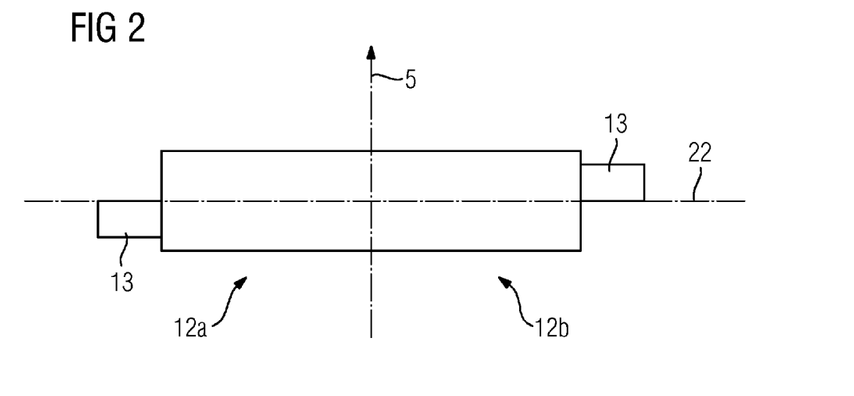

FIG. 2 shows an asymmetric X-ray detector 9, which can be used with the method according to an embodiment of the invention and the system according to an embodiment of the invention respectively.

The line-shaped X-ray detector 9 exhibits in this situation two detector regions 12a and 12b. At the left and right edges of the X-ray detector 9, i.e. at the left and right wide sides, the X-ray detector 9 exhibits asymmetrically-shaped side regions 13. The asymmetry relates here to the axis of rotation 5, which, expressed more precisely, is a projection of the axis of rotation 5 along a vertical 21 to the axis of rotation 5, starting from the X-ray emitter 8. The two side regions 13 are arranged on opposite wide sides of the X-ray detector 9. The side regions 13 exhibit a lesser expansion along the axis of rotation 5 than the maximum expansion of the individual detector regions 12a and 12b along the axis of rotation 5.

The side regions 13 are in each case arranged offset to the mid-line 22 along the wide side of the X-ray detector 9. In the example shown here, along the axis of rotation 5 the right side region 13 is displaced forwards and the left side region 13 backwards.

While the central region, including the detector regions 12a and 12b, can have, for example, a width of 64 lines (64-line CT device 1), the side regions 13 exhibit a width half the size, i.e. 32 lines.

In the example shown here, the central region, including the detector regions 12a and 12b, is formed symmetrically to the axis of rotation 5. In a further embodiment of the invention, however, the central region itself can also be formed asymmetrically in relation to the axis of rotation 5. In particular, the asymmetry can be attained without additional side regions 13, which are arranged offset to the mid-line 22. For example, the detector regions 12a and 12b can instead exhibit simply a different width, i.e. a different expansion along the mid-line 22 relative to the axis of rotation 5.

Figure 3:
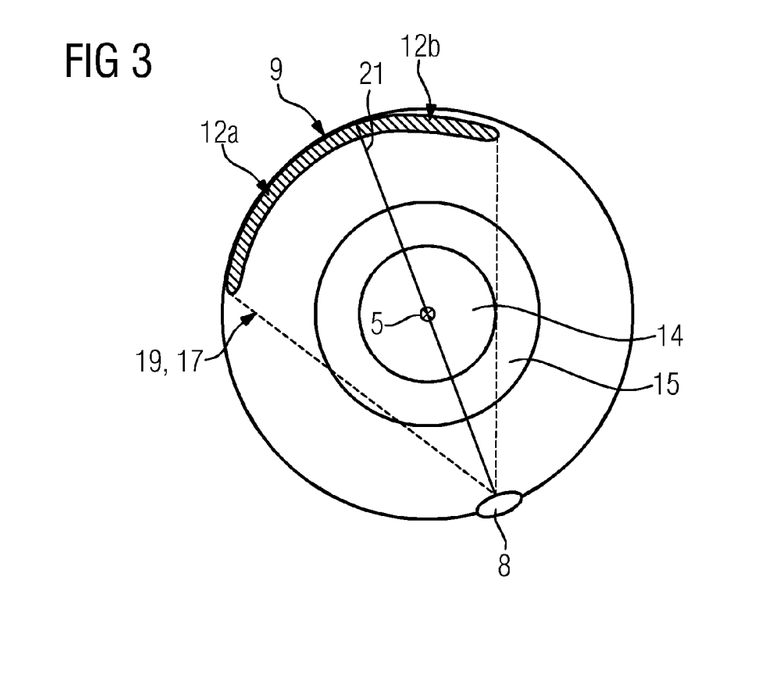

FIG. 3 shows a recording unit AE with the two projection regions 14 and 15 in cross-section. Such a recording unit AE can be used with the method according to an embodiment of the invention and the system according to an embodiment of the invention respectively.

The recording unit AE is rotatable about an axis of rotation 5, including an X-ray emitter 8 and an X-ray detector 9, which detects X-rays 17 from a fan-shaped region 19, wherein the fan-shaped region 19 is asymmetric in relation to a vertical 21 to the axis of rotation 5, running through the X-ray detector 9. In this situation, the two edges of the fan-shaped region 19, on rotation, in each case delimit an inner first projection region 14 and an outer second projection region 15 tangentially. The second projection region 15 abuts the first projection region 14. The second projection region 15 therefore encompasses the first projection region 14, but the first projection region 14 no longer belongs to the second projection region 15. The two projection regions are essentially circular and concentric to the axis of rotation 5. The two projection regions 14 and 15 can be formed cylindrically, i.e. extended along the axis of rotation 5, for example through the recording A with an X-ray detector 9 with a plurality of lines and/or through the recording A with a spiral scan. With a spiral scan, the recording unit AE rotates about its axis of rotation 5, which should coincide as precisely as possible with the longitudinal axis of the patient 3, while the patient couch 6 moves along the longitudinal axis of the patient 3 or the axis of rotation 5 respectively. In particular, such a spiral scan can be carried out with a pitch <0.5, such that, in the second projection region, a more complete data record can be recorded for each image point. The pitch is the ratio of the advance movement of the patient couch 6 per rotation of the recording unit AE in relation to the layer collimation of the X-rays 17.

In the example shown here, both the X-ray detector 9 as well as the fan-shaped region 19 of X-rays 17 are formed asymmetrically in relation to the vertical 21. To carry out the method according to the invention, however, it is sufficient if either the detection properties of the X-ray detector 9 or the fan-shaped region 19 of X-rays 17 are asymmetrical in relation to the vertical 21.

The method according to an embodiment of the invention is suitable for the imaging of a moved body part of a patient 3, in particular for the imaging of their heart. In the example shown here, the first projection region 14 exhibits a diameter of 35 centimeters, and the second projection region 15 an outer diameter of 50 centimeters, such that the heart is located entirely in the inner first projection region 14. Located in the outer second projection region 15 are, for example, moved lung structures.

Figure 4:
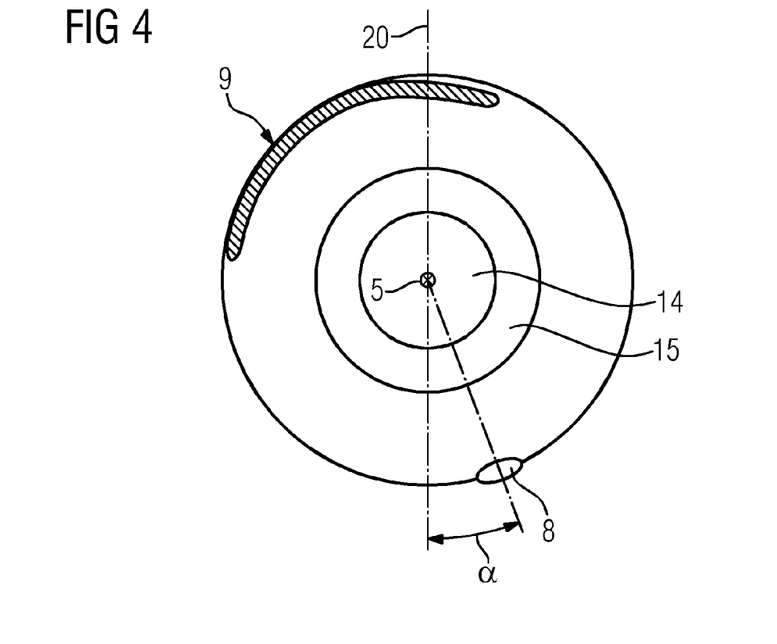

FIG. 4 shows a recording unit AE with a start angle $\alpha$ in cross-section.

To carry out the method according to an embodiment of the invention, X-ray projections of both the projection regions 14 and 15 are recorded, wherein the recording unit AE carries out at least one full rotation. During the full rotation, the recording unit AE covers a projection angle range of 360°. The term "projection angle" is understood to mean the relative angle between the recording unit AE and an axis selected at random in the rotation plane. An appropriate definition of the projection angle is, for example, the angle which encloses the vertical 21, which unambiguously characterizes the position of the recording unit AE during its rotation movement, with the vertical 20. During the rotation of the recording unit AE, therefore, X-ray projections are recorded from a plurality of different projection angles. In this situation, the X-ray projections which are allocated in each case to the different projection angles are recorded with a slight time skew, since the complete rotation of the recording unit AE typically lasts for half a second to one second.

The recording A of the projection data can be triggered by an EKG signal of a patient 3. Triggering of the recording A by an EKG signal is particularly suitable in the case of a recording A of the heart. This form of recording may, for example, be what is referred to as prospective EKG triggering. With an X-ray detector 9 extended appropriately along the axis of rotation 5, one individual rotation is adequate for the recording of the heart. The recording A can, however, also take place in the form of what is referred to as retrospective EKG gating.

In that case, a first image of the first projection region 14 is reconstructed by way of a reconstruction unit RE in such a way that the projection angle intervals for the reconstruction of the points in the first image in each case exhibit the same start angle $\alpha$ and therefore exhibit a concordant phase. In this situation, a projection angle interval which is used for a reconstruction is delimited by a start angle $\alpha$ and an end angle; in other words, the start angle $\alpha$ is a projection angle. The projection angle interval for the reconstruction of a first image R1 and the X-ray projections associated with it therefore begin for each point in the first image with the same projection angle. This is particularly important for the imaging of the heart, since the first image is then a phase-consistent representation of the heart.

In addition, a second image of the second projection region 15 is reconstructed by way of a reconstruction unit RE in such a way that the start angle $\alpha$ for the reconstruction of a point in the second image is selected on the basis of a projection angle interval and on the basis of the position of the respective point. The full rotation of the recording unit AE therefore also allows for the outer second projection region 15, which is only detected in part fan-shaped geometry, to be reconstructed in different ways, in particular with an optimized time resolution. Accordingly, the reconstruction of CT data of asymmetrically detected X-ray projections is extensively improved, such that the possibilities for the use of different reconstruction algorithms in the two projection regions are extended.

By way of an image processing unit BE, two reconstructed images can be merged to form one overall image of the two reconstruction regions 14 and 15. In particular, the first and the second image can be merged to form one overall image, which facilitates the interpretation of the images, in particular for diagnostic purposes.

In a further embodiment of the invention, in the reconstruction of a point in the second image, the projection angle interval is selected in such a way that all the projections to which the respective point contributes are used for the reconstruction of the point. Accordingly, the data quantity is maximized which is available for the reconstruction of a point in the second image.

FIGS. 5A to 5D show a recording unit with two different projection angle intervals in cross-section.

Figure 5A:
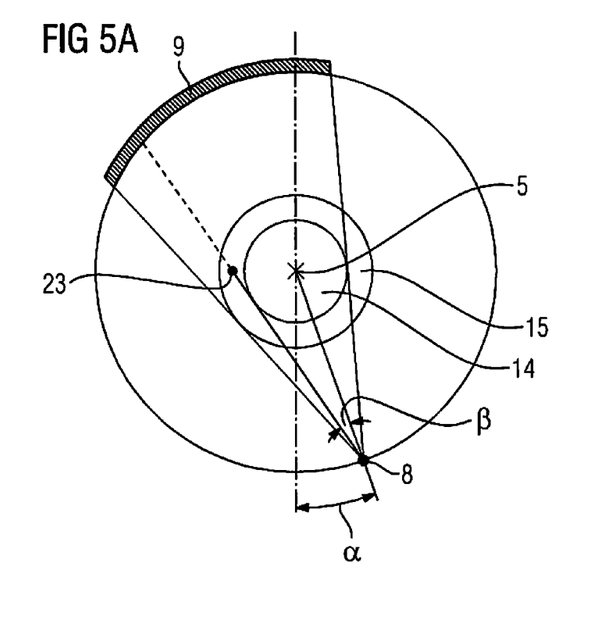
FIGS. 5A to 5D show a recording unit with two different projection angle intervals in cross-section,
FIG. 6 a method for tomographic imaging.
Figure 5B:
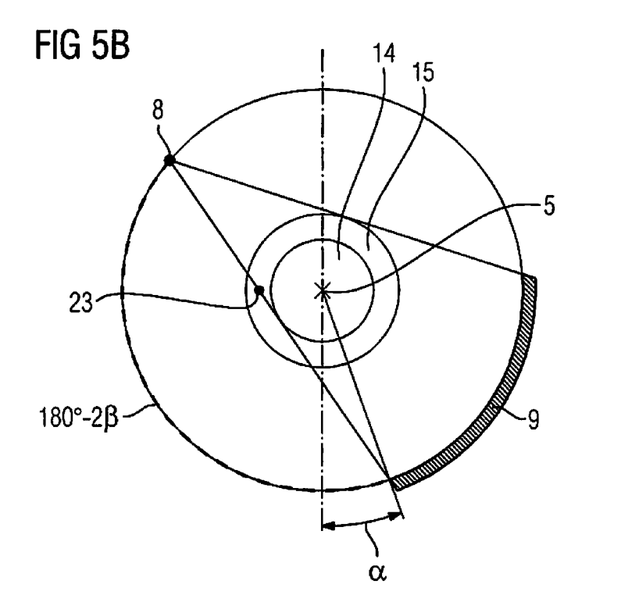

In a further embodiment of the invention, for the reconstruction of a point in the second image, the projection angle interval is delimited by two complementary projections of the respective point, and is selected as small as possible. In this case, the time resolution for the respective reconstructed point is optimized. The minimum projection angle interval is the smallest interval of projection angles which are necessary for the reconstruction of the respective point. The minimum projection angle interval comprises a range of (180°−2β) with an individual start angle $\alpha$ of the reconstruction which is dependent on the position of the point which is to be reconstructed. The angle β is the angle between the vertical 21 and an X-ray beam through the point 23 which is to be reconstructed with the selected start angle α. The time resolution for a point in the outer second reconstruction region 15 is optimized with reconstruction under a minimum projection angle interval, and amounts to trot·(180°-2β)/360°, wherein trot is the rotation time of the recording unit AE during the full rotation. The angle β for a point in the outer second reconstruction region 15 is also illustrated in FIGS. 5A and 5B.

Figure 5C:
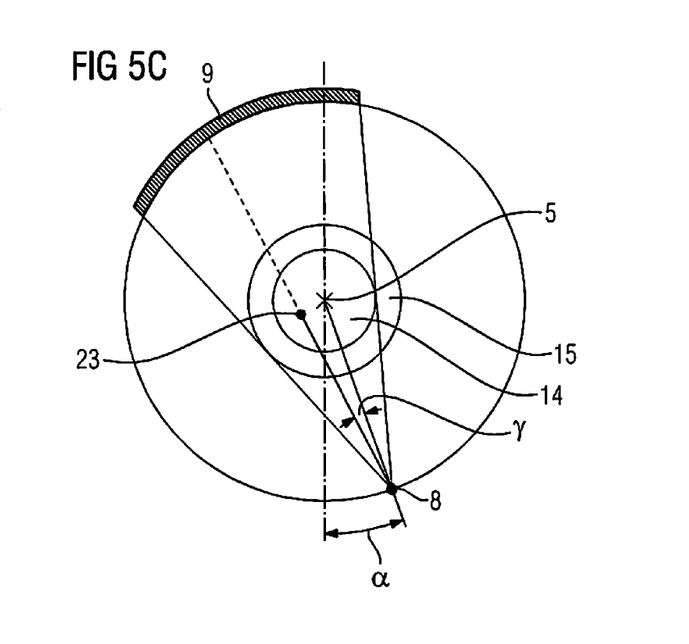
Figure 5D:
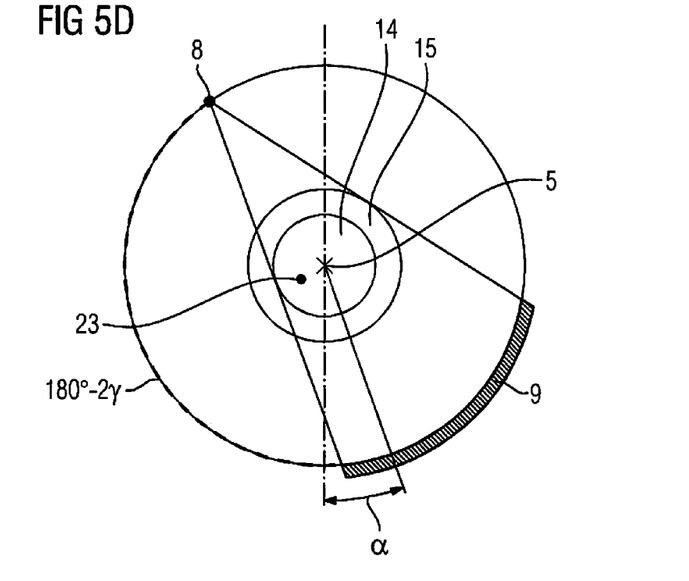

In a further embodiment of the invention, a third image of the first projection region 14 is reconstructed in such a way that the points in the third image are reconstructed with the aid of a minimum projection angle interval, such that they likewise exhibit an optimum time resolution. In this situation, the minimum projection angle interval used for the reconstruction is delimited in each case by two projection angles, under which complementary X-ray projections of the respective point are recorded. The minimum projection angle interval for a point 23 in the third image which is to be reconstructed comprises a range of (180°-2γ) with an individual start angle α of the reconstruction which is dependent on the position of the point which is to be reconstructed. The angle γ is the angle between the vertical 21 and an X-ray beam through the point 23 which is to be reconstructed with the selected start angle α. The angle γ for a point in the first reconstruction region 14 is also illustrated in FIGS. 5C and 5D.

In a further embodiment of the invention, the first and the third image are added together, in accordance with a weighting function, and the added image and the second image are then merged to form an overall image. In other words, the invention makes it possible for points in the first projection region, recorded under a full fan-shaped geometry, to be reconstructed a first time with the same phase and another time with optimized time resolution, and for these two reconstructions of the first projection region 14 to be added together, i.e. overlaid. The weighting function now allows for the determination of which points should exhibit a higher time resolution or a higher phase consistency respectively.

An embodiment of the invention further comprises that the weighting function weights points from the third image more heavily, as the distance interval from the axis of rotation 5 increases. If the second image of the second projection region and the third image of the first projection region have in each case been reconstructed with optimum time resolution, then it is possible, with the invention, for both projection regions to be reconstructed and merged in such a way that a continuous transition, as free of artefacts as possible, is obtained between the two projection regions.

An embodiment of the invention further comprises that several fourth images of the first projection region 14 are reconstructed in each case with different start angles α. The temporally-displaced fourth images can be drawn on for the optimization of the location of the reconstruction angle interval in the heart cycle of the patient 3, either by manual user interaction or automatically with known methods. Accordingly, more than only the minimum projection angle interval at recording angles is used for the reconstruction. The fourth images in the inner measuring field are reconstructed with slightly displaced start projections, i.e. in slightly displaced heart phases, in such a way that, finally, the entire data interval of 360° is used. The optimization of the location of the reconstruction interval in the heart cycle of the patient 3 is carried out in that the fourth image is selected, with the start angle α pertaining to it, which exhibits the highest image quality and the lowest movement artefacts. In particular, the optimum start angle α selected in this way can be used for the reconstruction of a first image R1 of the first projection region. Additionally, the fourth images can serve to reconstruct images in different heart phases, in order to make use of these for a functional evaluation.

Figure 6:
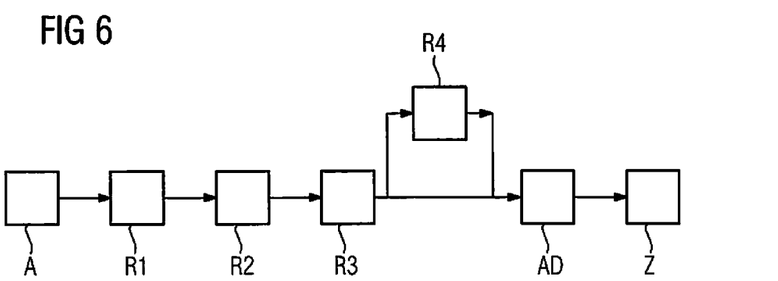

FIG. 6 shows a method for tomographic imaging. In particular, the extended system described in FIG. 1 is well-suited for the performance of this method. It makes use of the recording unit AE described in FIG. 1 to FIG. 5. The method comprises the following steps:

recording A of projection data of the first and of the second projection regions, wherein the recording unit AE carries out at least one full rotation, reconstruction of a first image R1 of the first projection region 14 in such a way that the projection angle interval for the reconstruction of the points in the first image in each exhibit the same start angle α, reconstruction of a second image R2 of the second projection region 15, wherein the start angle α for the reconstruction of a point in the second image is selected on the basis of a projection angle interval and on the basis of the position of the respective point, reconstruction of a third image R3 of the first projection region 14, reconstruction of several fourth images R4 of the first projection region 14, wherein, for the reconstruction of different fourth images, different start angles α are used in each case, adding AD together of the first and the third image in accordance with a weighting function, and merging Z of two reconstructed images to form one overall image of the first and second projection region.

Steps R1 to R4 can be carried out by means of the reconstruction unit RE described in FIG. 1, while steps AD and Z can be carried out by means of the image processing unit BE described in FIG. 1.

The invention can additionally be formed as a computer program with program code for carrying out the method according to the invention described heretofore, when the computer program is run on a computer 18. The computer program is configured in such a way that it can carry out specific method steps by means of a computer 18. In this situation, the computer 18 must in each case exhibit the preconditions required, such as, for example, an appropriate memory, an appropriate logic unit, and a connection to the recording unit AE, such that the respective method steps can be carried out efficiently.

Although the invention has been illustrated and described in close detail by way of the preferred exemplary embodiments, the invention is nevertheless not restricted by the disclosed examples, and other variations can be derived from them by the person skilled in the art without leaving the scope of protection of the invention. In particular, method steps can be carried out in sequences other than those described.

What is claimed is:

1. A method for tomographic imaging via a recording unit, rotatable about an axis of rotation, including an X-ray emitter and an X-ray detector arranged to detect X-rays from a fan-shaped region, wherein the fan-shaped region is asymmetrical in relation to a line orthogonal to the axis of rotation, the line running through the X-ray detector, wherein each of two edges of the fan-shaped region, on rotation, respectively delimit a first projection region and a second projection region tangentially, and wherein the second projection region abuts the first projection region, the method comprising:
  recording projections of the two projection regions, wherein the recording unit carries out at least one full rotation;
  reconstructing a first image of the first projection region such that the projection angle interval for each of the reconstruction of points in the first image, respectively exhibits a same start angle, the projection angle interval associated with respective ones of the points in the first image being an interval between two complementary projections of the respective ones of the points, the start angle for reconstruction of the first image being a first projection angle for the reconstruction of the points in the first image;
  reconstructing a second image of the second projection region, wherein the start angle for the reconstruction of a point in the second image is selected based on a projection angle interval and a position of the respective point, the projection angle interval associated with respective ones of the points in the second image being an interval between two complementary projections of the respective ones of the points, the start angle for the reconstruction of the second image being a first projection angle for the reconstruction of points the second image such that each of the plurality of points within the second projection region has its own start angle associated therewith; and
  merging the reconstructed first and second images to form one overall image of the first and second projection regions.

2. The method of claim 1, wherein, for the reconstruction of a point in the second image, the projection angle interval is selected such that all the projections to which the respective point contributes are used for the reconstruction of the point.

3. The method of claim 1, wherein, for the reconstruction of a point in the second image, the projection angle interval is delimited by two complementary projections of the respective point and is selected to be as small as possible.

4. The method of claim 2, wherein, for the reconstruction of a point in the second image, a length of the projection angle interval lies between lengths of the projection intervals as claimed in claim 2 and a projection angle interval delimited by two complementary projections of the respective point and selected to be as small as possible.

5. The method of claim 1, wherein the merging includes the first and second images being merged to form one overall image.

6. The method of claim 4, further comprising:
  reconstructing a third image of the first projection region, wherein, for the reconstruction of a point in the third image, the projection angle interval is selected in accordance with the projection angle interval as claimed in claim 4.

7. The method of claim 6, further comprising:
  adding together the first and third images in accordance with a weighting function, wherein the merging includes the added together image and the second image to form one overall image.

8. The method of claim 7, wherein the weighting function weights points from the third image more heavily as the distance interval from the axis of rotation increases.

9. The method of claim 6, further comprising:
  reconstructing several fourth images of the first projection region, wherein, for the reconstruction of different respective fourth images, different respective start angles are used.

10. The method of claim 1, wherein the recording takes place in the form of a spiral scan with a pitch <0.5.

11. The method of claim 1, wherein the recording is triggered by an EKG signal of a patient.

12. The method of claim 2, further comprising:
  reconstructing a third image of the first projection region, wherein, for the reconstruction of a point in the third image, the projection angle interval is selected in accordance with the projection angle interval as claimed in claim 2.

13. The method of claim 12, further comprising:
  adding together the first and third images in accordance with a weighting function, wherein the merging includes the added together image and the second image to form one overall image.

14. The method of claim 13, wherein the weighting function weights points from the third image more heavily as the distance interval from the axis of rotation increases.

15. A system for tomographic imaging, comprising:
  a recording unit, rotatable about an axis of rotation, including an X-ray emitter and including an X-ray detector arranged to detect X-rays from a fan-shaped region, wherein the fan-shaped region is asymmetric in relation to a line orthogonal to the axis of rotation, the line running through the X-ray detector, wherein two edges of the fan-shaped region, on rotation, each delimit a respective one of a first projection region and a second projection region tangentially, wherein the second projection region abuts the first projection region, and wherein the recording unit is configured to record projections from the two projection regions during at least one full rotation;
  a reconstruction unit, configured to,
    reconstruct a first image of the first projection region in such a way that a respective projection angle interval for the reconstruction of each of a plurality of points in the first image each exhibit a same start angle, the projection angle interval associated with respective ones of the points in the first image being an interval between two complementary projections of the respective ones of the points, the start angle for reconstruction of the first image being a first projection angle for the reconstruction of the points in the first image, and
    reconstruct a second image of the second projection region, wherein the start angle for the reconstruction of a respective point in the second image is selected based on a respective projection angle interval and a position of the respective point, the projection angle interval associated with respective ones of the points in the second image being an interval between two complementary projections of the respective ones of the points, the start angle for the reconstruction of the second image being a first projection angle for the reconstruction of points in the second image such that each of the plurality of points within the second projection region has its own start angle associated therewith; and
  an image processing unit, configured to merge two reconstructed images to form one overall image of the first and second projection regions.

16. The system of claim 15, wherein the X-ray detector is subdivided by the vertical into two at least one of differently shaped and different sized detector regions.

17. The system of claim 15, wherein at least one detector region exhibits, on a relatively wide side, a side region which exhibits a relatively lesser expansion in the direction of the axis of rotation than the remaining relatively larger part of the detector region.

18. The system of claim 15, arranged to carry out at least:
   recording projections of the two projection regions, wherein the recording unit carries out at least one full rotation;
   reconstructing a first image of the first projection region such that the projection angle interval for each of the reconstruction of points in the first image, respectively exhibits a same start angle;
   reconstructing a second image of the second projection region, wherein the start angle for the reconstruction of a point in the second image is selected on the basis of a projection angle interval and on the basis of the position of the respective point; and
   merging the reconstructed first and second images to form one overall image of the first and second projection regions.

19. The system of claim 16, wherein at least one detector region exhibits, on a relatively wide side, a side region which exhibits a relatively lesser expansion in the direction of the axis of rotation than the remaining relatively larger part of the detector region.

\* \* \* \* \*